US00PP11359P

United States Patent [19]

Salmon

[11] Patent Number: Plant 11,359

[45] Date of Patent: Apr. 25, 2000

[54] BRACHYCOME PLANT NAMED 'LEMON TWIST'

[75] Inventor: Alexander David Salmon, Gapsted, Australia

[73] Assignee: Outback Plants Pty. Ltd., The Patch, Australia

[21] Appl. No.: 09/177,285

[22] Filed: Oct. 22, 1998

[51] Int. Cl.[7] ..... A01H 5/00

[52] U.S. Cl. ..... Plt./263

[58] Field of Search ..... Plt./263

*Primary Examiner*—Howard J. Locker

*Assistant Examiner*—Kent L. Bell

*Attorney, Agent, or Firm*—C. A. Whealy

[57] ABSTRACT

A new and distinct cultivar of Brachycome plant named 'Lemon Twist', characterized by its compact and spreading growth habit; very freely branching plant habit, plants do not require pinching; numerous inflorescences with yellow ray florets; and erect peduncles that hold inflorescences above the foliage.

2 Drawing Sheets

BACKGROUND OF THE INVENTION

The present invention relates to a new and distinct cultivar of Brachycome plant, botanically known as *Brachycome multifida var. dilatata*×*Brachycome curvicarpa* and referred to by the cutlivar name 'Lemon Twist'. The new Brachycome is marketed under the trade name Mini Yellow.

The new Brachycome is a product of a planned breeding program conducted by the Inventor in Park Orchards, Victoria, Australia. The objective of the program is to create new compact Brachycome cultivars with large inflorescences that are suitable for a range of climatic conditions.

The new Brachycome originated from a cross by the Inventor of an unidentified selection of *Brachycome multifida var. dilatata*, as the female, or seed, parent with an unidentified selection of *Brachycome curvicarpa* as the male, or pollen, parent. The cultivar 'Lemon Twist' was discovered and selected by the Inventor as a flowering plant within the progeny of the stated cross in a controlled environment in Park Orchards, Victoria, Australia.

Asexual reproduction of the new Brachycome by terminal cuttings taken in a controlled environment in Park Orchards, Victoria, Australia, has shown that the unique features of this new Brachycome are stable and are reproduced true to type in successive generations.

SUMMARY OF THE INVENTION

The new Brachycome has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Lemon Twist' and distinguish 'Lemon Twist' as a new and distinct cultivar:

1. Compact and spreading growth habit.

2. Very freely branching plant habit, plants do not require pinching.

3. Numerous inflorescences with yellow ray florets.

4. Erect peduncles that hold inflorescences above the foliage.

Compared to plants of the female parent, an unidentified selection of *Brachycome multifida var. dilatata*, plants of the new Brachycome are more compact and differ in ray floret color.

Compared to plants of the male parent, an unidentified selection of *Brachycome curvicarpa*, plants of the new Brachycome are more compact, more spreading, and have shorter peduncles.

Plants of the new Brachycome can be compared to the Brachycome hybrid cultivar 'Sunburst', disclosed in U.S. Plant Pat. No. 10,203. However, in side-by-side comparisions conducted in Victoria, Australia, plants of the new Brachycome differ from plants of the cultivar 'Sunburst' in the following characteristics:

1. Plants of the new Brachycome are more compact than plants of the cultivar 'Sunburst'.

2. Plants of the new Brachycome have smaller leaves that are not as deeply lobed than plants of the cultivar 'Sunburst'.

3. Plants of the new Brachycome have smaller inflorescences than plants of the cultivar 'Sunburst'.

4. Ray floret color of plants of the new Brachycome is darker yellow than ray floret color of plants of the cultivar 'Sunburst'.

5. Plants of the new Brachycome have shorter peduncles than plants of the cultivar 'Sunburst'.

Plants of the new Brachycome can also be compared to the nonpatented Brachycome hybrid cultivar 'Lemon Drops'. However, in-side-by-side comparisions conducted in Victoria, Australia, plants of the new Brachycome differ from plants of the cultivar 'Lemon Drops' in the following characteristics:

1. Plants of the new Brachycome are more compact than plants of the cultivar 'Lemon Drops'.

2. Plants of the new Brachycome have larger inflorescences than plants of the cultivar 'Lemon Drops'.

3. Ray floret color of plants of the new Brachycome is brighter yellow than ray floret color of plants of the cultivar 'Lemon Drops'.

4. Ray floret color of plants of the new Brachycome does not fade as readily as ray floret color of plants of the cultivar 'Lemon Drops'.

BRIEF DESCRIPTION OF THE PHOTOGRAPHS

The accompanying colored photographs illustrate the overall appearance of the new Brachycome, showing the colors as true as it is reasonably possible to obtain in colored reproductions of this type.

The photograph on the first sheet comprises a side perspective view of a typical potted plant of 'Lemon Twist'.

The photograph on the second sheet comprises a close-up view of typical inflorescences of 'Lemon Twist'. Floret and foliage colors in the photographs may appear different from the actual colors due to light reflectance.

DETAILED BOTANICAL DESCRIPTION

The following observations, measurements, values, and comparisons describe plants grown in Victoria, Australia, under outdoor conditions with day temperatures ranging from 12 to 40° C., night temperatures ranging from 6 to 25° C., and light levels ranging from 5,000 to 9,000 footcandles. Color references are made to The Royal Horticultural Society Colour Chart except where general terms of ordinary dictionary significance are used.

Botanical classification: *Brachycome multifida var. dilatata*×*Brachycome curvicarpa* cultivar 'Lemon Twist'.

Parentage:

*Male or pollen parent.*—Unidentified selection of *Brachycome curvicarpa.*

*Female or seed parent.*—Unidentified selection of *Brachycome multifida var. dilatata.*

Propagation:

*Type.*—By cuttings.

*Time to initiate and develop roots.*—Summer: About 10 to 20 days at temperatures of 25° C. Winter: About 15 to 30 days to temperatures of 20° C.

*Rooting habit.*—Fine, fibrous and freely branching.

Plant description:

*General appearance.*—Compact, upright and spreading, flat to somewhat rounded herbaceous plant with erect peduncles. Suitable for 10 to 15-cm containers and hanging baskets. To produce a 15-cm finished flowering plant from rooted cuttings, 10 to 14 weeks are required depending on temperature and light level.

*Plant height.*—About 10 to 25 cm from soil level to top of inflorescences.

*Plant diameter or spread.*—About 25 to 40 cm.

*Branching.*—Very freely branching, numerous lateral branches develop even without removal (pinching) of the terminal apices.

*Growth rate/vigor.*—Moderate.

*Stem description.*—Lateral branch length: About 5 to 10 cm. Lateral branch diameter: About 1 mm. Internode length: About 0.4 to 2.1 cm. Texture: Glabrous. Color: 137C.

*Foliage description.*—Arrangement: Alternate, single. Quantity: About 9 to 27 per lateral branch. Shape: Narrowly oblanceolate to narrowly pinnatifid. Apex: Two to three-lobed. Base: Sessile, long-tapering. Length: About 2.8 cm. Width: About 4 mm. Margin: Sparsely toothed or shallow lobed. Texture: Glabrous, smooth, thin. Color: Young leaves, upper surface: 137B. Young leaves, lower surface: 137D. Fully expanded leaves, upper surface: 137A; venation, 137A. Fully expanded leaves, lower surface: 137B; venation, 137B.

Flowering description:

*Inflorescence.*—Single daisy-type composite inflorescence form. Florets arranged acropetally on a capitulum. Inflorescences last on the plant for about 2 to 3 weeks and about 5 to 7 days as a fresh cut flower. Self-cleaning.

*Natural flowering season.*—Natural flowering season is spring to fall; flowering continuous during this period.

*Response time.*—About 4 to 6 weeks.

*Quantity of inflorescences.*—About one to five per lateral branch with numerous inflorescences per plant.

*Inflorescence diameter.*—About 1.7 cm.

*Inflorescence depth (height).*—About 5 to 6 mm.

*Disc diameter.*—About 6–7 mm.

*Inflorescence aspect.*—Flat during the day with ray florets becoming somewhat reflexed at night.

*Rate of inflorescence opening.*—About 5 to 10 days.

*Fragrance.*—Very faint, honey-like.

*Inflorescence buds.*—Shape: Flattened spherical. Length: About 2 mm. Diameter: About 4 mm. Color: 146A.

*Ray florets.*—Quantity: About 29 to 43 florets per inflorescence arranged in one to two rows. Shape: Narrowly oblanceolate. Apex: Obcordate or notched. Base: Attenuate. Margin: Entire. Aspect: Flat. Length: About 5 to 7 mm. Width: About 1 to 1.5 mm. Texture: Smooth, glabrous, thin. Color: When opening, upper surface: 5A. When opening, lower surface: 22A. Mature, upper surface: 3B, with further development, floret color fades to 5C. Mature, lower surface: 4B.

*Disc florets.*—Shape: Tubular with five lobes. Length: About 2 mm. Width: Less than 1 mm. Texture: Sparsely pubescent. Color: Immature: 152D. Mature: 7A. Number of disc florets per inflorescence: Numerous.

*Peduncle.*—Length: About 6.2 cm. Strength: Flexible, moderate strength; erect and straight. Texture: Smooth, glabrous. Color: 144A.

*Involucral bracts.*—Arrangement: Imbricate. Quantity: About 18 to 28 per inflorescence. Shape: Oblong, slightly keeled and concave. Apex: Pointed to rounded, fringed. Margin: Entire and fringed. Texture: Somewhat fleshy; slightly pubescent. Color: 137C; pinkish margins.

*Androecium.*—Only present on disc florets. Stamen number: Five per disc floret. Anther shape: Oblong to linear. Anther color: 152C. Amount of pollen: Scarce. Pollen color: 152C.

*Gynoecium.*—Pistil number: One per floret. Stigma shape: Bilobate. Style length: About 2 mm. Style color: 152C. Stigma color: 1C.

Disease resistance: May be susceptible to Botrytis and fungal leaf spot diseases.

Seed production: Seed production has not been observed.

It is claimed:

1. A new and distinct cultivar of Brachycome plant named 'Lemon Twist', as illustrated and described.

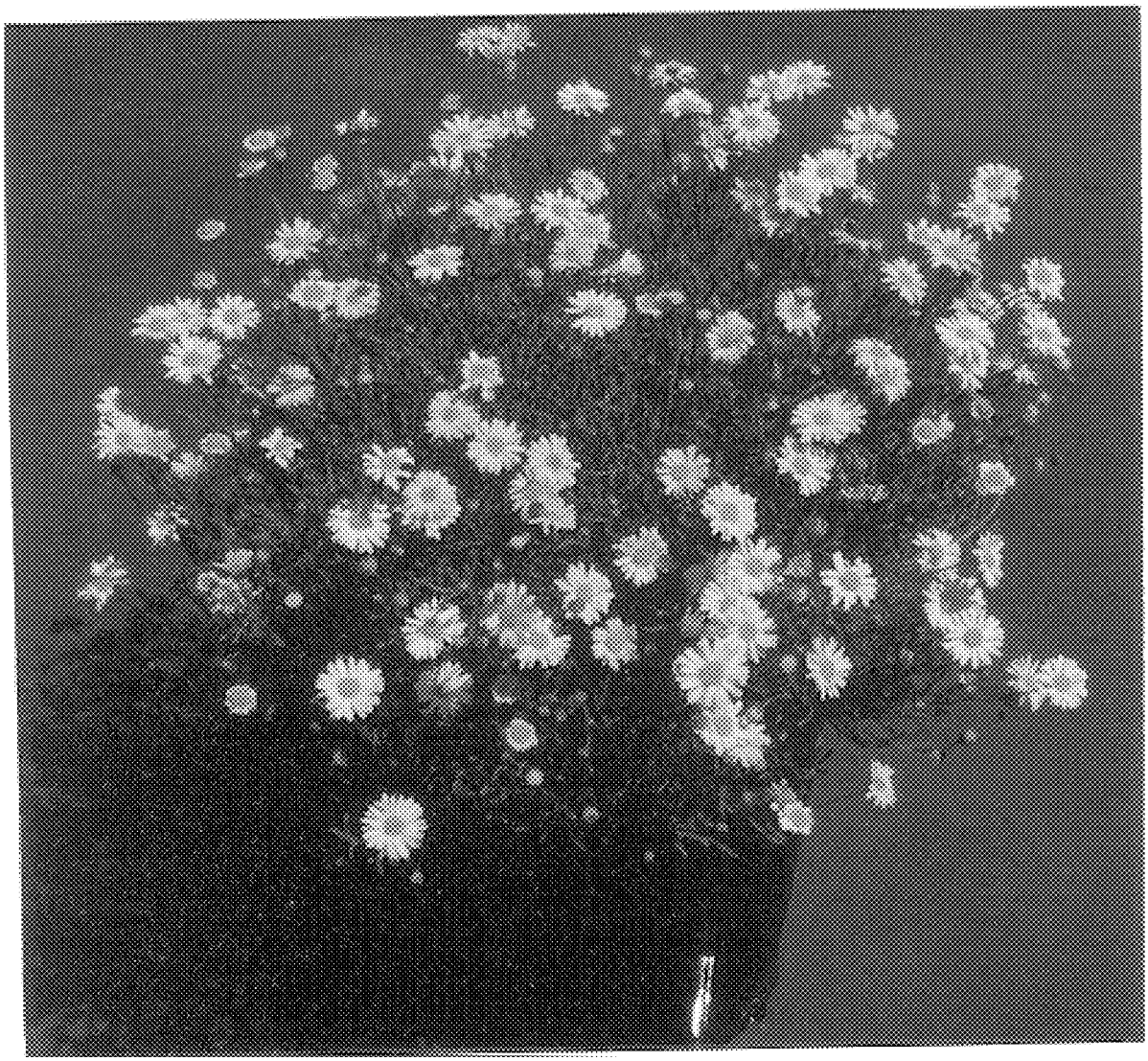

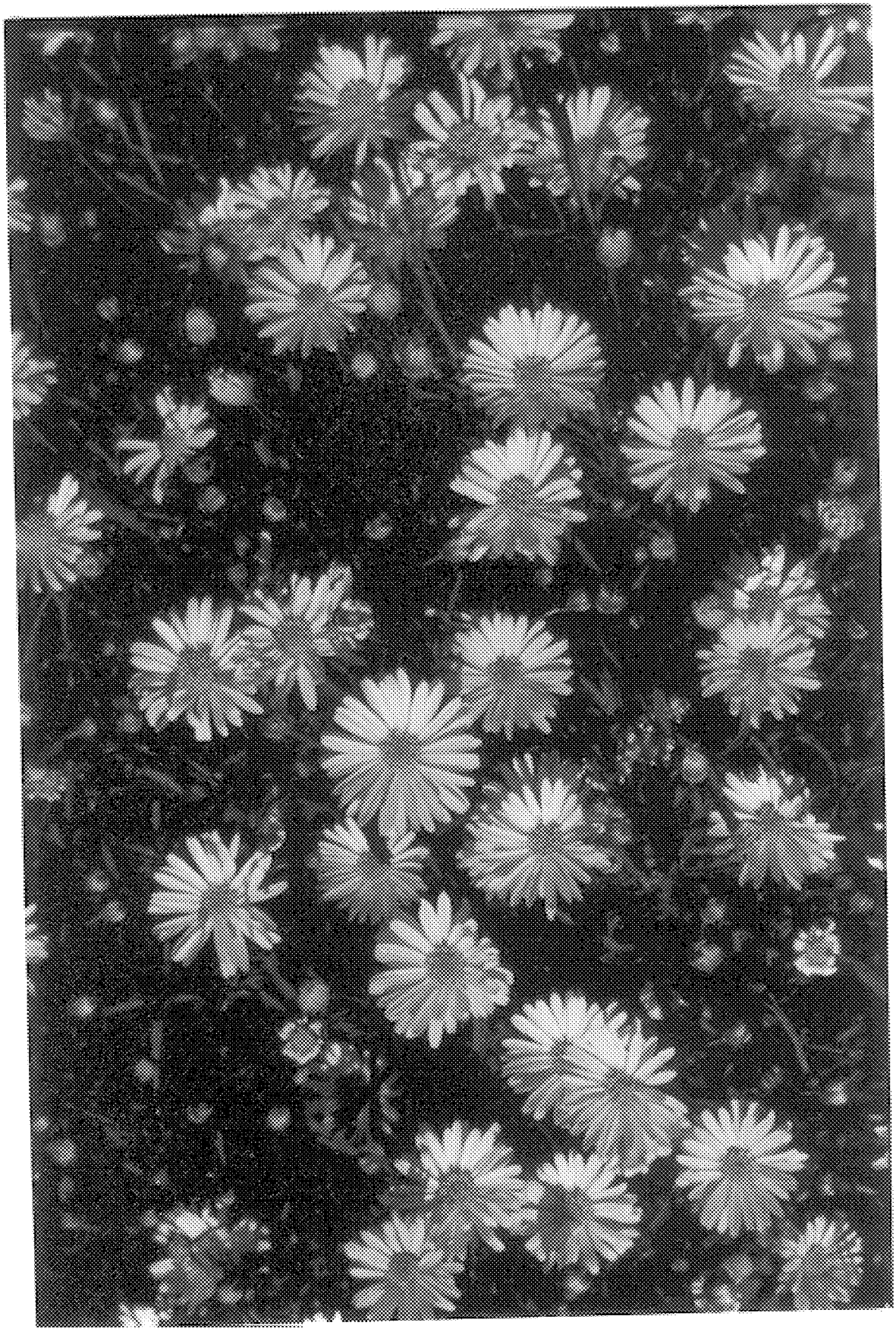

* * * * *